(12) United States Patent
Bryan et al.

(10) Patent No.: US 7,641,692 B2
(45) Date of Patent: Jan. 5, 2010

(54) IMPLANTABLE JOINT PROSTHESIS

(75) Inventors: Vincent Bryan, Mercer Island, WA (US); Alex Kunzler, Issaquah, WA (US); Charles R. Clark, Mercer Island, WA (US); Robert Conta, Mercer Island, WA (US); Carlos E. Gil, Sammamish, WA (US)

(73) Assignee: Warsaw Orthopedic, Inc.

( * ) Notice: Subject to any disclaimer, the term of this patent is extended or adjusted under 35 U.S.C. 154(b) by 1693 days.

(21) Appl. No.: 09/924,298

(22) Filed: Aug. 8, 2001

(65) Prior Publication Data

US 2002/0128715 A1    Sep. 12, 2002

Related U.S. Application Data

(63) Continuation of application No. 09/783,910, filed on Feb. 13, 2001, now abandoned.

(60) Provisional application No. 60/265,218, filed on Jan. 31, 2001, provisional application No. 60/223,863, filed on Aug. 8, 2000.

(51) Int. Cl.
*A61F 2/44* (2006.01)

(52) U.S. Cl. .................................................. 623/17.15

(58) Field of Classification Search .............. 623/16.11, 623/17.11–17.16
See application file for complete search history.

(56) References Cited

U.S. PATENT DOCUMENTS

| | | | |
|---|---|---|---|
| 2,677,369 A | 5/1954 | Knowles | |
| 3,486,505 A | 12/1969 | Morrison | |
| 3,864,758 A * | 2/1975 | Yakich | 623/22.13 |
| 3,875,595 A | 4/1975 | Froning | |
| 3,876,728 A | 4/1975 | Kuroda et al. | |
| 4,023,572 A | 5/1977 | Weigand et al. | |
| 4,116,200 A | 9/1978 | Braun et al. | |
| 4,179,810 A | 12/1979 | Kirsch | |
| 4,193,139 A * | 3/1980 | Walker | 623/21.17 |
| 4,309,777 A | 1/1982 | Patil | |
| 4,313,232 A * | 2/1982 | Habal et al. | 128/898 |

(Continued)

FOREIGN PATENT DOCUMENTS

DE    2263842    7/1974

(Continued)

OTHER PUBLICATIONS

Brain et al.; "The Neurological Manifestations of Cervical Spondylosis;" Brain: A Journal of Neurology, vol. 75; Macmillan & Co.; 1952; pp. 187-225.

(Continued)

*Primary Examiner*—Pedro Philogene

(57) ABSTRACT

The invention relates to a surgical implant that provides an artificial diarthroidal-like D joint, suitable for use in replacing any joint, but particularly suitable for use as an intervertebral disc endoprosthesis. The invention contains two rigid opposing shells, each having an outer surface adapted to engage the surfaces of the bones of a joint in such a way that the shells are immobilized by friction between their outer surfaces and the surfaces of the bone. These outer surfaces are sufficiently rough, while the inner surfaces of the shells are relatively smooth. The central body has a shape that cooperates with the shape of the inner surface of the shell so as to provide a range of motion similar to that provided by a healthy joint.

37 Claims, 6 Drawing Sheets

U.S. PATENT DOCUMENTS

| | | | |
|---|---|---|---|
| 4,314,380 A * | 2/1982 | Miyata et al. | 623/23.61 |
| 4,349,921 A | 9/1982 | Kuntz | |
| 4,599,086 A | 7/1986 | Doty | |
| 4,645,507 A | 2/1987 | Engelbrecht et al. | |
| 4,714,469 A | 12/1987 | Kenna | |
| 4,743,256 A | 5/1988 | Brantigan | |
| 4,757,983 A | 7/1988 | Ray et al. | |
| 4,759,766 A * | 7/1988 | Buettner-Janz et al. | 623/17.15 |
| 4,759,769 A | 7/1988 | Hedman et al. | |
| 4,766,328 A | 8/1988 | Yang | |
| 4,777,942 A | 10/1988 | Frey et al. | |
| 4,800,639 A | 1/1989 | Frey et al. | |
| 4,834,757 A | 5/1989 | Brantigan | |
| 4,863,476 A | 9/1989 | Shepperd | |
| 4,863,477 A | 9/1989 | Monson | |
| 4,874,389 A | 10/1989 | Downey | |
| 4,878,915 A | 11/1989 | Brantigan | |
| 4,887,595 A | 12/1989 | Heinig et al. | |
| 4,904,260 A | 2/1990 | Ray et al. | |
| 4,904,261 A | 2/1990 | Dove et al. | |
| 4,908,032 A | 3/1990 | Keller | |
| 4,908,036 A | 3/1990 | Link et al. | |
| 4,911,718 A | 3/1990 | Lee et al. | |
| 4,917,704 A | 4/1990 | Frey et al. | |
| 4,932,969 A * | 6/1990 | Frey et al. | 623/17.12 |
| 4,932,975 A | 6/1990 | Main et al. | |
| 4,946,378 A | 8/1990 | Hirayama et al. | |
| 4,955,908 A | 9/1990 | Frey et al. | |
| 4,978,355 A | 12/1990 | Frey et al. | |
| 4,990,163 A * | 2/1991 | Ducheyne et al. | 427/2.24 |
| 4,997,432 A | 3/1991 | Keller | |
| 5,002,576 A * | 3/1991 | Fuhrmann et al. | 623/17.15 |
| 5,015,247 A | 5/1991 | Michelson | |
| 5,035,716 A | 7/1991 | Downey | |
| 5,047,055 A | 9/1991 | Bao et al. | |
| 5,059,193 A | 10/1991 | Kuslich | |
| 5,059,194 A | 10/1991 | Michelson | |
| 5,062,845 A | 11/1991 | Kuslich et al. | |
| 5,071,437 A | 12/1991 | Steffee | |
| 5,080,662 A | 1/1992 | Paul | |
| 5,084,048 A | 1/1992 | Jacob et al. | |
| 5,108,438 A | 4/1992 | Stone | |
| 5,122,130 A | 6/1992 | Keller | |
| 5,123,926 A | 6/1992 | Pisharodi | |
| 5,171,280 A | 12/1992 | Baumgartner | |
| 5,171,281 A | 12/1992 | Parsons et al. | |
| 5,176,708 A | 1/1993 | Frey et al. | |
| 5,192,326 A | 3/1993 | Bao et al. | |
| 5,192,327 A | 3/1993 | Brantigan | |
| 5,219,363 A * | 6/1993 | Crowninshield et al. | 623/23.34 |
| 5,234,431 A | 8/1993 | Keller | |
| 5,236,460 A | 8/1993 | Barber | |
| 5,246,458 A | 9/1993 | Graham | |
| 5,258,031 A | 11/1993 | Salib et al. | |
| 5,261,911 A | 11/1993 | Carl | |
| 5,261,913 A | 11/1993 | Marnay | |
| 5,306,308 A | 4/1994 | Gross et al. | |
| 5,314,477 A | 5/1994 | Marnay | |
| 5,314,478 A | 5/1994 | Oka et al. | |
| 5,320,644 A | 6/1994 | Baumgartner | |
| 5,370,697 A | 12/1994 | Baumgartner | |
| 5,383,933 A | 1/1995 | Keller | |
| 5,401,269 A * | 3/1995 | Buttner-Janz et al. | 623/17.15 |
| 5,403,314 A | 4/1995 | Currier | |
| 5,425,772 A | 6/1995 | Brantigan | |
| 5,425,773 A | 6/1995 | Boyd et al. | |
| 5,443,514 A | 8/1995 | Steffee | |
| 5,456,719 A | 10/1995 | Keller | |
| 5,458,638 A | 10/1995 | Kuslich et al. | |
| 5,458,642 A | 10/1995 | Beer et al. | |
| 5,484,437 A | 1/1996 | Michelson | |
| 5,489,307 A | 2/1996 | Kuslich et al. | |
| 5,489,308 A | 2/1996 | Kuslich et al. | |
| 5,496,318 A | 3/1996 | Howland et al. | |
| 5,507,816 A | 4/1996 | Bullivant | |
| 5,514,180 A | 5/1996 | Heggeness et al. | |
| 5,527,315 A | 6/1996 | Jeanson et al. | |
| 5,534,028 A | 7/1996 | Bao et al. | |
| 5,534,029 A | 7/1996 | Shima | |
| 5,534,030 A * | 7/1996 | Navarro et al. | 623/17.15 |
| 5,534,090 A | 7/1996 | Leining | |
| 5,545,229 A | 8/1996 | Parsons et al. | |
| 5,549,679 A | 8/1996 | Kuslich | |
| 5,556,431 A * | 9/1996 | Buttner-Janz | 623/17.15 |
| 5,562,738 A | 10/1996 | Boyd et al. | |
| 5,571,189 A | 11/1996 | Kuslich | |
| 5,593,409 A | 1/1997 | Michelson | |
| 5,593,445 A * | 1/1997 | Waits | 623/23.42 |
| 5,609,636 A | 3/1997 | Kohrs et al. | |
| 5,641,323 A * | 6/1997 | Caldarise | 623/22.18 |
| 5,645,597 A * | 7/1997 | Krapiva | 606/61 |
| 5,645,598 A | 7/1997 | Brosnahan | |
| 5,649,926 A | 7/1997 | Howland | |
| 5,658,285 A | 8/1997 | Marnay et al. | |
| 5,662,158 A | 9/1997 | Caldarise | |
| 5,674,294 A * | 10/1997 | Bainville et al. | 623/17.16 |
| 5,674,295 A | 10/1997 | Ray et al. | |
| 5,674,296 A * | 10/1997 | Bryan et al. | 623/17.16 |
| 5,676,701 A | 10/1997 | Yuan et al. | |
| 5,683,464 A | 11/1997 | Wagner et al. | |
| 5,702,450 A | 12/1997 | Bisserie | |
| 5,713,899 A | 2/1998 | Marnay et al. | |
| 5,716,415 A | 2/1998 | Steffee | |
| 5,720,748 A | 2/1998 | Kuslich et al. | |
| 5,722,977 A | 3/1998 | Wilhelmy | |
| 5,723,013 A | 3/1998 | Jeanson et al. | |
| 5,741,253 A | 4/1998 | Michelson | |
| 5,782,830 A | 7/1998 | Farris | |
| 5,782,832 A | 7/1998 | Larsen et al. | |
| 5,797,909 A | 8/1998 | Michelson | |
| 5,824,093 A | 10/1998 | Ray et al. | |
| 5,824,094 A | 10/1998 | Serhan et al. | |
| 5,865,846 A | 2/1999 | Bryan et al. | |
| 5,865,848 A | 2/1999 | Baker | |
| 5,868,796 A * | 2/1999 | Buechel et al. | 623/16.11 |
| 5,885,300 A | 3/1999 | Tokuhashi et al. | |
| 5,888,197 A | 3/1999 | Mulac et al. | |
| 5,888,226 A | 3/1999 | Rogozinski | |
| 5,897,087 A | 4/1999 | Farley | |
| 5,902,233 A | 5/1999 | Farley et al. | |
| 5,928,284 A | 7/1999 | Mehdizadeh | |
| 5,947,971 A | 9/1999 | Kuslich et al. | |
| 5,976,187 A | 11/1999 | Richelsoph | |
| 5,984,865 A | 11/1999 | Farley et al. | |
| 5,989,291 A * | 11/1999 | Ralph et al. | 623/17.15 |
| 6,001,130 A | 12/1999 | Bryan et al. | |
| 6,017,008 A | 1/2000 | Farley | |
| 6,022,376 A | 2/2000 | Assell | |
| 6,033,363 A | 3/2000 | Farley et al. | |
| 6,059,790 A | 5/2000 | Sand et al. | |
| 6,059,829 A | 5/2000 | Schlapfer et al. | |
| 6,063,121 A | 5/2000 | Xavier et al. | |
| 6,066,174 A | 5/2000 | Farris | |
| 6,080,155 A | 6/2000 | Michelson | |
| 6,083,228 A | 7/2000 | Michelson | |
| 6,086,595 A | 7/2000 | Yonemura et al. | |
| 6,096,038 A | 8/2000 | Michelson | |
| 6,096,084 A * | 8/2000 | Townley | 623/23.12 |
| 6,132,465 A * | 10/2000 | Ray et al. | 623/17.16 |
| 6,139,579 A | 10/2000 | Steffee et al. | |
| 6,156,067 A | 12/2000 | Bryan et al. | |
| 6,162,252 A | 12/2000 | Kuras et al. | |
| 6,179,874 B1 | 1/2001 | Cauthen | |
| 6,228,022 B1 | 5/2001 | Friesem et al. | |

| | | | |
|---|---|---|---|
| 6,228,026 B1 | 5/2001 | Rullo et al. | |
| 6,231,609 B1 * | 5/2001 | Mehdizadeh | 623/17.11 |
| 6,283,998 B1 * | 9/2001 | Eaton | 623/17.16 |
| 6,290,726 B1 | 9/2001 | Pope et al. | |
| 6,348,071 B1 * | 2/2002 | Steffee et al. | 623/17.15 |
| 6,395,032 B1 * | 5/2002 | Gauchet | 623/17.12 |
| 6,395,034 B1 | 5/2002 | Suddaby | |
| 6,402,785 B1 * | 6/2002 | Zdeblick et al. | 623/17.16 |
| 6,533,817 B1 * | 3/2003 | Norton et al. | 623/17.16 |
| 6,582,466 B1 * | 6/2003 | Gauchet | 623/17.11 |
| 6,682,562 B2 * | 1/2004 | Viart et al. | 623/17.14 |
| 6,723,127 B2 | 4/2004 | Ralph et al. | |
| 7,250,060 B2 | 7/2007 | Trieu | |
| 2002/0183848 A1 * | 12/2002 | Ray et al. | 623/17.12 |
| 2005/0251260 A1 | 11/2005 | Gerber et al. | |

FOREIGN PATENT DOCUMENTS

| | | | |
|---|---|---|---|
| DE | 2804936 | | 8/1979 |
| DE | 30 23 353 A1 | | 4/1981 |
| DE | 3343863 | * | 6/1985 |
| DE | 37 41 493 A1 | | 6/1989 |
| DE | 90 00 094.3 | | 4/1990 |
| DE | 9000094.3 | | 4/1990 |
| EP | 0176728 | | 4/1986 |
| EP | 00560140 A1 | | 9/1993 |
| FR | 2805985 | * | 3/2000 ............... 623/17.14 |
| SU | 895433 | | 1/1982 |
| SU | 1560184 | | 4/1990 |
| WO | WO 93/16656 | * | 9/1993 |
| WO | WO 00/04839 | | 2/2000 |
| WO | WO 00/04851 | | 3/2000 |
| WO | WO 00/13619 | | 3/2000 |
| WO | WO 00/13620 | | 3/2000 |

OTHER PUBLICATIONS

Buttner-Janz et al.; "Biomechanics of the SB Charite Lumbar Intervertebral Disc Endoprosthesis;" International Orthopedics; vol. 13; 1989; pp. 173-176.
Edeland; "Some Additional Suggestions for an Intervertebral Disc Prosthesis;" Dept. of Occupational Health; Vdvo PV AB; S-40508; Goteborg; Sweden; 1985 Butterworth & Co. Publishers Ltd.
Enker et al.; "Artificial Disc Replacement;" Spine; vol. 18; No. 8; 1993; pp. 1061-1070.
Hawkins et al.; "Shear Stability of an Elastomeric Disk Spacer Within an Intervertebral Joint: A Parametric Study;" Journal of Biomechanical Engineering Technical Briefs; vol. 114, Aug. 1992; pp. 414-415.
Hedman et al.; "Design of an Intervertebral Disc Prosthesis;" Spine; vol. 17; No. 6; 1991; pp. S256-S260.
Hellier et al.; "Wear Studies for Development of an Intervertebral Disc Prosthesis;" Spine; vol. 17; No. 6 Supplement; 1992; pp. S86-S96.
Hodd; "Far Lateral Lumbar Disc Herniations;" Neurosurgery Clinics of North America; vol. 4, No. 1; Jan. 1993; pp. 117-124.
Langrana et al.; "Finite-Element Modeling of the Synthetic Intevertebral Disc;" Spine; vol. 16; No. 6: 1991; pp. S245-S252.
Lee et al.; "Development of a Prosthetic Intervertebral Disc;" Spine; vol. 16; No. 6; 1991; pp. S253-S255.
Lee et al.; "Natural History & Prognosis of Cervical Spondylosis;" British Medical Journal; Dec. 28, 1963; British Medical Association, London, England; Copyright 1963; pp. 1607-1610.
Long; "Failed Back Surgery Syndrome;" Neurosurgery Clinics of North America; vol. 2, No. 4; Oct. 1991; pp. 899-919.
Ray; "The Artificial Disc—Introduction, History and Socioeconomics;" Clinical Efficacy and Outcome in the Diagnosis and Treatment of Low Back Pain; Raven Press, Ltd., NY; 1992; pp. 205-280.
Robinson et al.; The Results of Anterior Interbody Fusion of the Cervical Spine, The Journal of Bone & Joint Surgery; vol. 44-A, No. 8, Dec. 1962; pp. 1569-1587.
Simeone and Rothman; "Cervical Disc Disease;" Pennsylvania Hospital & University of Pennsylvania; 1975; pp. 387-433.
Solini et al.; "Metal Cementless Prosthesis for Vertebral Body Replacement of Metastatic Malignant Disease of the Cervical Spine;" Journal of Spinal Disorders; vol. 2; No. 4; 1989; pp. 254-262.
Solini et al.; "Protesi Somatica Cervicale;" Ingegneria Ricostruttiva D'Avanguardia; Howmedica International; Pfizer; Italy.
Taylor, Collier;, "The Occurrence of Optic Neuritis in Lesions of the Spinal Cord, Injury, Tumor, Melitis;" Brain: A Journal of Neurology; vol. 24; Macmillian & Co. Ltd., 1901; pp. 532-550.
Tie-sheng et al.; "Lumbar Intervertebral Disc Prosthesis;" Chinese Medical Journal, 104-(5); 1991; pp. 381-386.
Artificial Disc, Market Potential and Technology Update, Viscogliosi Bros., LLC, Feb. 2000, pp. 1-65.
Boning-Up, The Musculoskeletal Healthcare Industry, Industry Commentary & Review of 1999, Viscogliosi Bros., LLC, Mar. 10, 2000, pp. 1-33.
Bryan Total Cervical Disc Prosthesis, Single Level Surgical Technique Manual, SPINALdynamics Corporation, 2000, 01080-004, pp. 29.
Morphology of the Human Skeleton, pp. 268270; 283-291; 315-331; 489-495.
Spine Industry Dynamics, Viscogliosi Bros., LLC, Mar. 10, 2000, pp. 1-4.
International Search Report for International Application No. PCT/US 01/24791.

* cited by examiner

IMPLANTABLE JOINT PROSTHESIS

This application is a continuation of Ser. No. 09/783,910, filed Feb. 13, 2001, now abandoned which claims benefit under 35 U.S.C. §119(e) of Provisional U.S. Ser. No. 60/223,863, filed 8 Aug. 2000, and entitled INSTRUMENTATION AND METHOD FOR IMPLANTING A PROSTHETIC INTERVERTEBRAL BODY and of Provisional U.S. Ser. No. 60/265,218 entitled GRAVITY ASSISTED LOCALIZATION SYSTEM, filed Jan. 31, 2001.

BACKGROUND OF THE INVENTION

1. Field of the Invention

The invention relates to implantable prostheses that are suitable for replacement of diarthroidal or arthroidal joints by creating an artificial diarthroidal-like joint at the site of the implant.

In a particular embodiment, the invention relates to implantable prostheses serving as replacements for at least a portion of the intervertebral disc material, i.e., a spinal disc endoprostheses suitable for implantation in vertebrates, including humans.

2. Description of Related Art

Many joints in the human body, such as hips, knees, shoulders, etc., are diarthroidal, meaning that the joints include a joint capsule that is filled with fluid. The capsule fluid lubricates the joint, and allows the surfaces of the joint to move with a low coefficient of friction. The spine, by contrast, can be considered to be a series of joints, some of which (the anterior joint or disc) lack a fluid filled capsule and are therefore arthroidal (the spine also contains facet joints that are diarthroidal). The interior portion of intervertebral discs are not provided by the body with significant blood supply; their homeostasis is enhanced by the diffusion of fluids into the disc tissue, thus supplying them with nutrients. This, to some extent, allows the tissue to grow and repair damage done by stress as the joint moves. Despite this process, in mature adults, spinal disc tissue degrades continuously over time. Sufficiently advanced degeneration can lead to herniation or rupture of the spinal disc.

Herniation of a spinal disc can result in a number of debilitating symptoms, including intractable pain, weakness, and sensory loss. Treatment of these symptoms frequently requires surgical removal of at least a portion of the herniated disc, a procedure known as discectomy. Often discectomy alone cannot stop the progressive degeneration at the level of disc excision. An additional procedure is often performed in conjunction with the discectomy with the objective of fusing together (arthrodesis) the vertebral bodies surrounding the affected disc space. This is accomplished by removing the cartilaginous endplates by scraping the surfaces of the vertebral body and inserting a piece of graft bone, which may be an allograft from a bone bank, or an autograft, typically taken from the iliac crest of the patient, or other suitable material.

The discectomy and arthrodesis procedures can be problematic, however. Discectomy problems have been described above. The grafting or fusion procedure has a variable success rate of about 80%, and even when successful, requires considerable recovery time before fusion is complete. Perhaps of even greater concern, successful fusion eliminates normal spinal biomechanics. Range of motion at the level of the fusion is ideally eliminated, because the affected vertebrae have been effectively joined to form a single bone. Because the patient tries to maintain the same overall range of motion of the entire spine, additional stress is imposed on the intervertebral discs of the adjacent vertebrae. This, in turn, may lead to accelerated degeneration at levels above and below the fusion site, which may require additional treatment, including discectomy and fusion. Grafting procedures carry some risk of tissue rejection and disease, transmission if an allograft is used, and risk of harvest site morbidity when the patient's own tissue is harvested.

As a result of these difficulties with intervertebral fusion, attempts have been made to provide a prosthetic solution to degenerative disc disease that maintains the patient's normal spinal biomechanics, allows for shorter recovery times, and avoids the complications inherent in harvesting and/or grafting bone tissue. Some of these efforts have centered around providing an endoprosthetic intervertebral implant, as described in U.S. Pat. Nos. 5,865,846, 5,674,296, 5,989,291, 6,001,130, and 6,022,376, the entire contents of each of which is hereby incorporated by reference.

Design and construction of such an implant, however, is not simple. Desirably, the implant should be precisely placed in a prepared intervertebral space, and should contain elements that are immobilized with respect to each of the vertebral bodies, so that the implant does not migrate or shift, potentially contacting, abrading, or otherwise damaging the spinal cord, ligaments, blood vessels, and other soft tissue. At the same time, the implant should allow the vertebral bodies to move relative to each other in a way that provides the equivalent motion afforded by a healthy intervertebral disc, and that allows the affected vertebral joint to participate in the coordinated overall movement of the spine in a way that closely approximates the natural movement of a healthy spinal column. The implant should be biocompatible, and avoid the introduction of toxic or harmful components into the patient, such as release of wear debris. The implant should also restore normal disc height and maintain the patient's vertebral lordosis, and should not allow any significant postoperative subsidence. The implant should be at least partially constrained by soft tissue in and around the intervertebral space, in order to allow a simpler, more efficient design. There remains a need for a device which would decrease patient recovery time, and reduce the occurrence of postoperative degeneration at levels above and below the implant, as compared with fusion techniques. In addition, such an implant would avoid the need for harvesting of autograft bone tissue, thereby eliminating morbidity at the harvesting site. Such an implant should also provide elasticity and damping sufficient to absorb shocks and stresses imposed on it in a manner similar to that of the natural spinal disc.

SUMMARY OF THE INVENTION

This invention satisfies the needs and concerns described above. Other concerns can arise that are more unique to any joint replacement or reconstruction, particularly with respect to device stability, range of motion, and postoperative material degradation. In general, in patients undergoing joint replacement, the patient's condition and quality of life is improved more by a technique that provides a range of motion that more closely approximates the range of motion of a healthy joint (assuming that this can be done in a safe manner) than by a technique that provides a decreased range of motion. Important parts of accomplishing this goal include using an implant design that is highly stable when implanted, and making use of the soft tissue associated with the joint (to the extent possible) to stabilize the implant and leave restriction of some of the motion of the joint to the soft tissue. This allows the implant design to be considerably simpler. Irrespective of the joint being implanted, an implant that provides an effectively sealed, fluid filled capsule (i.e., an artificial diarthroidal-like joint) will likely provide an added margin of safety because the moving surfaces are isolated from the surrounding tissue and body fluids, and the environment in which the moving surfaces operate can be engineered and controlled. The lubrication effects in such a joint allow it to function more effectively and potentially generate less wear debris. Any wear debris that is generated, however, is contained within the implant and will not come into contact with live tissue or body fluids. Similarly, tissue ingrowth into the articulating regions of the implant and degradation of the implant materials by body fluids are also avoided.

In one aspect, the invention can be viewed as a surgical implant where the structure of the implant contains cooperating features that allows a joint into which the implant has been inserted to closely approximate the biomechanics and motion of a healthy joint.

In this aspect, the invention contains two rigid opposing plates or shells, each having an outer surface adapted to engage the prepared surfaces of the bones of a Joint in such a way that frictional forces resist movement of the plates or shells relative to the bone surface. The outer surfaces are sufficiently rough that frictional forces strongly resist any slippage between the outer surface and the bone surfaces in the joint. In addition to providing surface friction at the interface with the bone, the outer surfaces may be adapted to allow for bony ingrowth, which acts to further stabilize the plates or shells in place over time. The inner surfaces of the plates or shells are relatively smooth, and adapted to slide easily with low friction across a portion of the outer surface of an elastically deformable, resilient central body disposed between the plates or shells. Desirably, the inner surfaces have an average roughness of about 1 to about 8 microinches, more particularly less than about 3 microinches. The central body has a shape that cooperates with the shape of the inner surface of the plate or shell so as to provide motion similar to that provided by a healthy joint.

The surgical implant of the invention provides exceptional stability, because the roughened outer surfaces of the plates or shells and their geometric shape supply sufficient frictional force to keep the implant from slipping from its proper position on the surfaces of the bones forming the joint. In addition, the geometry of the outer surfaces and the prepared surfaces of the bone cooperate to contain the implant between the bone surfaces. The smooth inner surfaces of the rigid opposing plates or shells are shaped to cooperate and articulate with the shape of the smooth surface of the deformable resilient central body to allow relatively unconstrained motion of the plates or shells with respect to the resilient central body until the limit of acceptable motion is reached. Once the limit of allowable motion is reached, the shape of the inner surface of the plate or shell cooperates with the shape of the deformable resilient central body to effectively resist any movement beyond the desired motion. This allows the motion of a joint containing the implant to closely approximate the motion provided in a healthy joint, alleviating undesirable stresses imposed on the joint or bone structure, or in the case of a vertebral implant, on adjacent joints as well. This, in turn, reduces the likelihood of further joint degeneration in adjacent joints.

The deformable resilient central body also provides elasticity and dampening properties, similar to those provided by healthy joint tissue. It is also sufficiently creep-resistant or resistant to plastic deformation to avoid post-operative loss of disc space height and to maintain appropriate joint geometry. The surface of the central body is hard, in some embodiments harder than the interior, which provides good wear resistance. It is also very lubricious, which provides good tribological properties in conjunction with the inner surfaces of the rigid plates or shells.

The resulting implant is safe because it can be implanted with precision, and once implanted, it is stable. It is extremely effective because the geometry of the internal surfaces is configured to provide a range of motion that closely approximates that provided by healthy joint tissue, thus allowing coordinated movement of the spine and reducing stress on adjacent joints.

In another aspect, the invention relates to an implant that effectively provides an artificial diarthroidal-like joint, suitable for use in replacing any joint, but particularly suitable for use as an intervertebral disc endoprosthesis. In this aspect, the implant contains, in addition to the opposing rigid plates or shells and deformable, resilient central body described above, a flexible sleeve or sheath that extends between edges of the opposing plates or shells.

The inner surface of this sheath, together with the inner surfaces of the rigid plates or shells, defines a cavity surrounding the central body. Most, if not all, of the interior space of this cavity can be filled with a fluid lubricant, further decreasing the frictional force between inner surfaces of the plates or shell and the surface of the central body, again within the constraints of allowable motion.

The flexible sleeve or sheath serves to hold the implant together as a single unit, making it easier to manipulate during the implant procedure. It also retains the lubricant within the implant and provides a contained, sealed environment that keeps tissue from entering the interior of the implant, isolates the central body from possible attack or degradation by body fluids, and prevents any wear debris that might be generated from exiting the implant and migrating into surrounding tissues. The implant therefore provides a sealed capsule presenting only biocompatible surfaces to surrounding tissues, and keeping wear surfaces internal to the implant and permanently lubricated. The result is an implant with extremely good durability, because the articulating surfaces have been isolated away from the natural bone surfaces and placed in a lubricated capsule.

In yet another aspect, the invention provides a vertebral endoprosthesis, having:

an upper and a lower rigid, opposed, biocompatible plate or shell, each comprising:
  an outer, rough surface;
  an inner, smooth surface; and
  an edge between the surfaces;
  wherein the inner smooth surface of at least one of the plates or shells comprises a first motion limiting device;

a deformable, resilient central body disposed between the inner, smooth surfaces of the upper and lower plates or shells, comprising:
  a smooth upper surface adjacent to the inner smooth surface of the upper plate or shell and a smooth lower surface adjacent to the inner smooth surface of the lower plate or shell;
  a second motion limiting device disposed on at least one of the smooth upper and lower surfaces adapted to contact the first motion limiting device and limit the relative motion of the plate or shell with respect to the central body.

The inner surfaces of the plates or shells can desirably be concave, and articulate with smooth upper surfaces of the deformable resilient central body that are convex. This arrangement creates, in effect, an artificial ball-and-socket-like joint in the intervertebral space, which joint is inherently stable under compression.

In a more specific embodiment of this aspect of the invention, the vertebral endoprosthesis contains:

an upper and a lower rigid, opposed biocompatible concavo-convex shell, each comprising:
an outer, rough convex surface, comprising a porous coating of a biocompatible material;
an inner concave surface, comprising:
a smooth contact area; and
an axial post extending toward the opposing shell; and
an edge between the surfaces, comprising:
a circumferential groove adapted to receive a retaining ring;
a first ridge circumscribing the contact area of the inner concave surface and extending axially toward the opposing shell;
an insertion tab extending axially away from the opposing shell, and comprising an opening adapted to releasably engage a tool for manipulating, inserting, or removing the endoprosthesis;
a closable passage between the outer surface and the inner surface of the shell;
a deformable, resilient central body disposed between the inner, smooth concave surfaces of the upper and lower shells, comprising:
smooth convex upper and lower surfaces complementary and adjacent to the smooth contact area of the inner surfaces of the respective upper and lower shells;
a second ridge circumscribing each of the smooth convex upper and lower surfaces and adapted to contact the first ridge of the adjacent shell and limit the relative motion of the shell with respect to the central body;
a laterally extending equatorial ridge disposed between the first ridge of the upper concavo-convex shell and the first ridge of the lower concavo-convex shell;
an opening in the upper and lower convex contact surfaces adapted to receive the axial post of the inner surface of each shell;
an elastic sheath or sleeve disposed between the upper and lower shells and surrounding the central body, comprising an inner surface, an outer surface, an upper edge attached to the upper shell, and a lower edge attached to the lower shell, wherein the inner surface of the sheath and the inner surfaces of the shells define an enclosing cavity;
an upper retaining ring of a biocompatible material disposed in the circumferential groove in the upper concavo-convex shell and securing the upper edge of the elastic sheath or sleeve to the shell and a lower retaining ring of a biocompatible material disposed in the circumferential groove of the lower concavo-convex shell and securing the lower edge of the sheath or sleeve to the shell.

This endoprosthesis provides the advantages described above with respect to the more general aspects of the invention, and more specifically provides an implantable vertebral joint that approximates the disc height and range of motion of a healthy intervertebral disc, with significantly increased durability relative to natural intervertebral disc material, and without the drawbacks of spinal fusion.

In addition, the concavo-convex geometry of the opposing shells, and the precise preparation of a mating concave surface in the vertebral body endplates, into which the convex outer surfaces of the shells are inset, provide a highly stable implanted joint. Coupled with the roughness provided by the porous coating on the outer surface of the shell, this inset shape holds the implant firmly in place so that it cannot migrate and come into contact with nerves or blood vessels, and so that the desired bony ingrowth can occur. The convex outer surface also provides additional surface area that contacts cancellous bone, increasing both the opportunity for bony ingrowth and the frictional force holding the shells in place. The mating of the concave inner surfaces of the shells with the curved shape of the central body provides a simple ball-and-socket-like system that is inherently highly stable under compression, as it will be when implanted. The embodiment of the invention using concavo-convex shells and a convex surface on the deformable central body therefore provides immediate mechanical stability.

Because the range of motion provided by the implant closely approximates that of a healthy disc, post-operative adjacent level disc degeneration is minimized or avoided entirely. In addition, the implant does not significantly constrain joint torsion, but instead relies on the remaining soft tissue (e.g., remaining disc annulus, ligaments, etc.) in and around the implanted joint to provide appropriate torsional constraint. Neither the shapes of the plates or shells or of the central body, or of the central retaining posts or central axial opening restrict the torsional movement of the shells relative to the central body (i.e., the rotation of the shells or of the central body about a central axis. This is of benefit because it significantly decreases the stress imposed on the interface between the bone surfaces and the outer surfaces of the implant, making movement of these implant surfaces relative to the bone less likely. This, in turn, increases the likelihood of bony ingrowth instead of fibrous tissue formation, and therefore increases long-term stability.

BRIEF DESCRIPTION OF DRAWINGS

The invention can be more clearly understood by reference to the following drawings, which illustrate specific embodiments thereof, and which are not intended to limit the scope of the appended claims.

FIG. 1 is a plan view (A) and sectional view (B) of one embodiment of an intervertebral endoprosthesis of the invention undergoing lateral bending.

Figure 1:
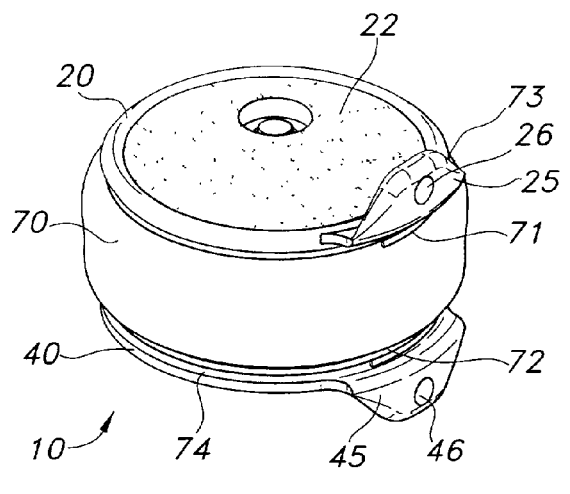
FIG. 1 is a perspective drawing of an intervertebral endoprosthesis in accordance with a specific embodiment of the invention.
Figure 3:
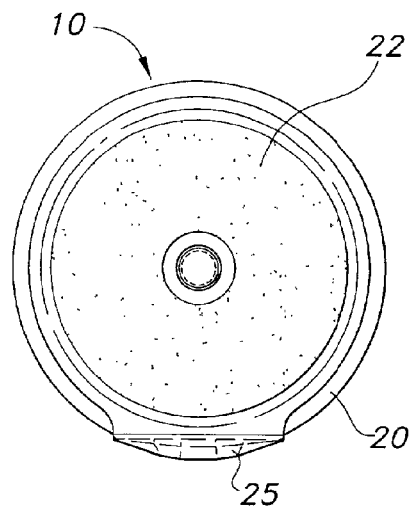
FIG. 3 is a top plan view of the intervertebral endoprosthesis shown in FIGS. 1 and 2.
Figure 2:
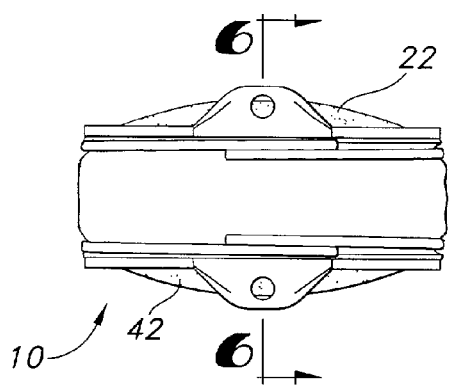
FIG. 2 is an elevational view of the intervertebral endoprosthesis shown in FIG. 1.

The invention can be more clearly understood by reference to some of its specific embodiments, described in detail below, which description is not intended to limit the scope of the claims in any way.

DETAILED DESCRIPTION OF SPECIFIC EMBODIMENTS

In broad aspect, the size and shape of the implant are substantially variable, and this variation will depend upon the joint geometry. Moreover, implants of a particular shape can be produced in a range of sizes, so that a surgeon can select the appropriate size prior to or during surgery, depending upon his assessment of the joint geometry of the patient, typically made by assessing the joint using CT, MRI, fluoroscopy, or other imaging techniques.

The rigid opposing plates or shells can be made of any rigid, biocompatible material, but are generally made of a biocompatible metal, such as stainless steel, cobalt chrome, ceramics, such as those including $Al_2O_3$ or $Zr_2O_3$, or titanium alloy. ASTM F-136 titanium alloy has been found to be particularly suitable. As indicated above, the outer surface of the rigid opposing plates or shells are rough, in order to restrict motion of the shells relative to the bone surfaces that are in contact with the plates. This is particularly important in the time period just after implantation (the "acute" phase of healing), since excessive movement of the implant relative to the bone can result in the formation of fibrous tissue between the bone and the implant, rather than the bony ingrowth, which is desirable for long term implant stability (i.e., during the "chronic" phase of healing). It has been discovered that a porous coating formed from nonspherical sintered beads provides very high friction between the outer surface of the shell and the bone, as well as providing an excellent interaction with the cancellous bone of the joint, increasing the chances of bony ingrowth. One example of a suitable nonspherical sintered bead coating is that made of pure titanium, such as ASTM F-67. The coating can be formed by vacuum sintering.

At least a portion of the inner surface of each plate or shell is smooth, and of a shape that complements and articulates with the shape of at least a portion of the central body. This smoothness and correspondence in shape provides unconstrained movement of the plate or shell relative to the central body, provided that this movement occurs within the allowable range of motion.

The structural features of the shapes of the inner surface of the plate or shell and the central body that interact to limit the movement to this allowable range will necessarily vary to some extent, based on the joint in which the implant will be used. As an example, the edge of the plate or shell can be extended toward the central body, so as to for a wall that, under shear, can contact a ridge or shoulder formed in the surface of the central body. This will allow for unconstrained motion of the plate or shell except in a direction that will bring the extension into contact with the ridge. By forming the extension around the entire edge of the shell, and by forming a ridge or shoulder that encloses a portion of the surface of the central body, translational, flexural, extensional, and lateral motion of the plate or shell relative to the central body can be constrained in all directions. Those of skill in the art will recognize that a bead or ridge at other locations on the inner surface of the plate or shell will serve a similar purpose, and that the location of this bead or ridge, as well as the ridge or stop on the central body, can be varied between implants for different joints, in order to obtain the desired range of motion for that particular joint.

The plates may be identical, which is desirable for ease of manufacture, or may be of different design (shape, size, and/or materials) to achieve different mechanical results. For example, differing plate or shell sizes may be used to more closely tailor the implant to a patient's anatomy, or to shift the center of rotation in the cephalad or caudal direction.

In a more particular embodiment, the inner surface of the shell and the outer surface of the central body can contain complementary structures that will function as an expulsion stop, so that the central body cannot be expelled from between the opposing plates or shells when the plates or shells are at maximum range of motion in flexion/extension. Examples of such structures include a post and corresponding hole to receive the post. The hole can have a diameter sufficiently large that relative motion between the shells and central body is unconstrained within the allowable range of motion, but that will nevertheless cause the post to arrest the central body before it is expelled from the implant under extreme compression. Alternatively, the diameter of the post may be such that it limits the translational movement of the central body during normal motion of the spine by contacting the surface of the hole in the central body at the limit of the allowable range of motion for the device. The elastically deformable, resilient central body may also vary somewhat in shape, size, composition, and physical properties, depending upon the particular joint for which the implant is intended. The shape of the central body should complement that of the inner surface of the shell to allow for a range of translational, flexural, extensional, and rotational motion, and lateral bending appropriate to the particular joint being replaced. The thickness and physical properties of the central body should provide for the desired degree of elasticity or damping. Accordingly, an elastomeric material is typically used for the central body. However, the central body should be sufficiently stiff to effectively cooperate with the shell surfaces to limit motion beyond the allowable range. The surface of the central body should be sufficiently hard to provide acceptable wear characteristics. One way to achieve this combination of properties is to prepare a central body having surface regions that are harder than the material of the central body closer to its core. The central body is therefore desirably a biocompatible elastomeric material having a hardened surface. Polyurethane-containing elastomeric copolymers, such as polycarbonate-polyurethane elastomeric copolymers and polyether-polyurethane elastomeric copolymers, generally having durometer ranging from about 80A to about 65D (based upon raw, unmolded resin) have been found to be particularly suitable for vertebral applications. If desired, these materials may be coated or impregnated with substances to increase their hardness or lubricity, or both. Examples of suitable materials are provided in more detail below.

The shape of the central body may also be designed to prevent contact between the edges of the rigid opposing shells during extreme motion of the implant. For example, a ridge or lip in the region of the central body between the shells and extending laterally can provide a buffer, preventing contact between the shells. This prevents friction and wear between the shells, thereby avoiding the production of particulates, which could cause increased wear on the internal surfaces of the implant.

In a particular embodiment, one or both of the rigid opposing shells can be provided with an opening therein, in the form of a passage between the outer and inner surfaces. When the implant is partially assembled, i.e., the deformable resilient central body has been disposed between the rigid opposing shells, and the sheath has been attached to the edges of the shells, the passage can be used to introduce liquid lubricant into the implant. The passage can then be closed off (e.g., by filing it with an appropriately sized plug), thereby providing a sealed, lubricant filled inner cavity.

Attachment of the sheath to the rigid, opposing shells can be accomplished in a variety of ways. Typically the rigid opposing shell is made from a biocompatible metallic alloy, e.g., a titanium alloy, while the sheath is typically made from an elastomeric polymeric material, such as segmented polyurethane. Attachment of the sheath to the shell can be accomplished by providing the edge of the rigid shell with a circumferential groove (the term "circumferential" in this context does not imply any particular geometry). The groove is of a shape and depth sufficient to accept a retaining ring, typically made of a biocompatible weldable wire, such as stainless steel or titanium. The sheath can be disposed so that it overlaps the circumferential groove, and the retaining ring formed by wrapping the wire around the groove over the overlapping portion of the sheath, cutting the wire to the appropriate size, and welding the ends of the wire to form a ring. Laser welding has been found to be particularly suitable in this regard.

The invention as described above can be used as a prosthetic implant in a wide variety of joints, including hips, knees, shoulders, etc. The description below focuses on an embodiment of the invention wherein the implant is a spinal disc endoprosthesis, but similar principles apply to adapt the implant for use in other joints. Those of skill in the art will readily appreciate that the particulars of the internal geometry will likely require modification from the description below to prepare an implant for use in other joints. However, the concept of using a core body having geometric features adapted to interact with inner surfaces of opposing shells to provide relatively unconstrained movement of the respective surfaces until the allowable range of motion has been reached, and the concept of encasing these surfaces in a fluid filled capsule formed by the opposing shells and a flexible sheath, are applicable to use in any joint implant.

Reference is made below to the drawings, which shall now be used to illustrate a specific embodiment of the present invention, namely a spinal disc endoprosthesis.

Figure 4:
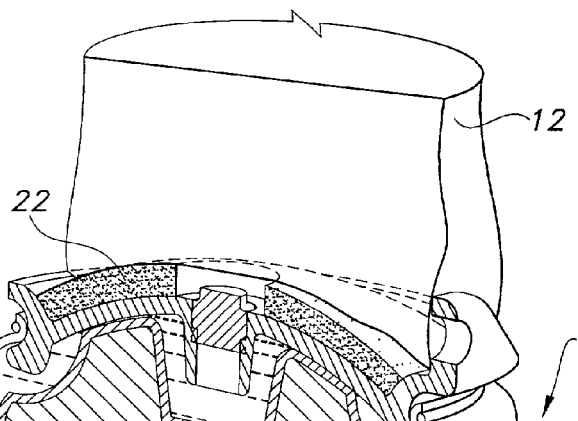
FIG. 4 is an isometric cross sectional view of the intervertebral endoprosthesis shown in FIGS. 1, 2, and 3.
Figure 7:
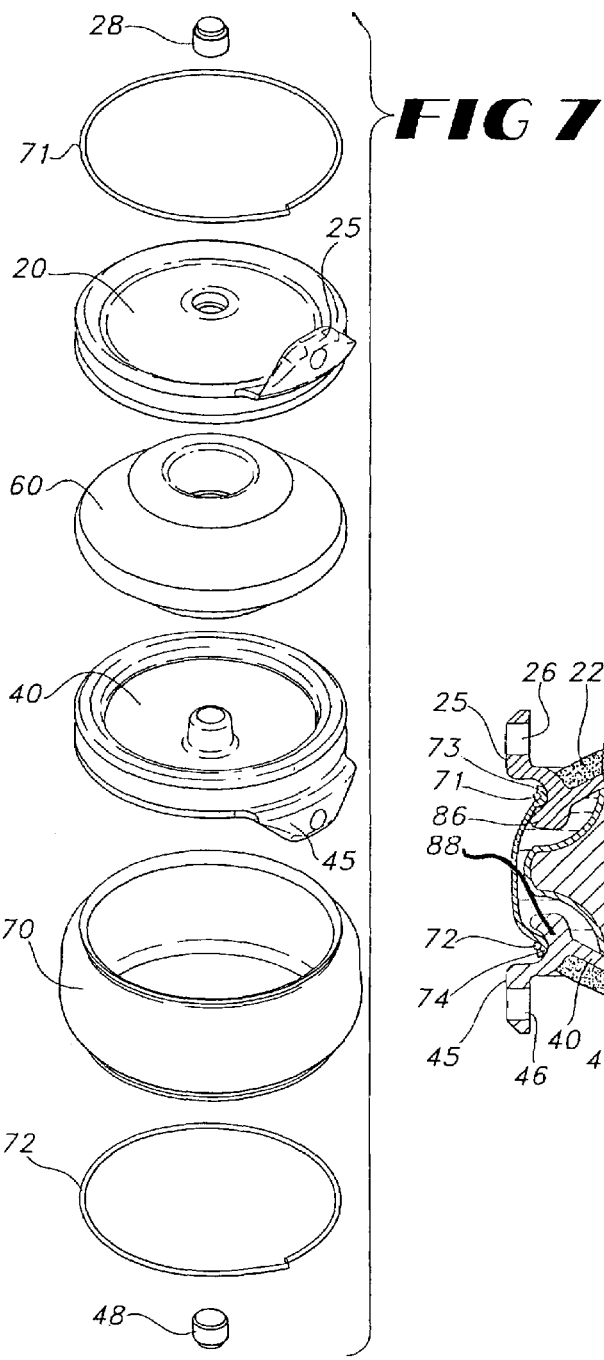
FIG. 7 is an exploded perspective view of the intervertebral endoprosthesis shown in FIGS. 14 and 6.
Figure 6:
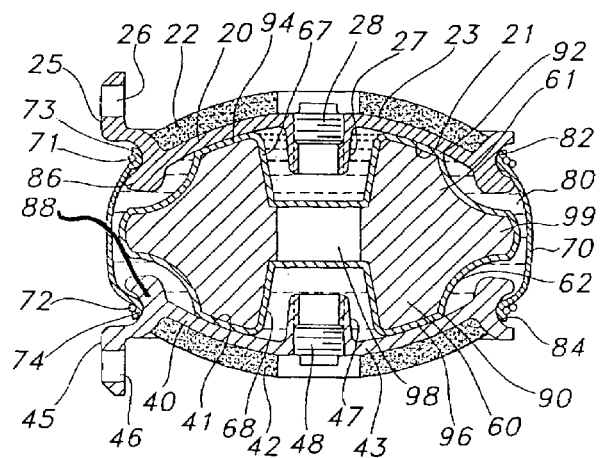
FIG. 6 is a sectional view of the intervertebral endoprosthesis shown in FIGS. 1-4.
Figure 8A:
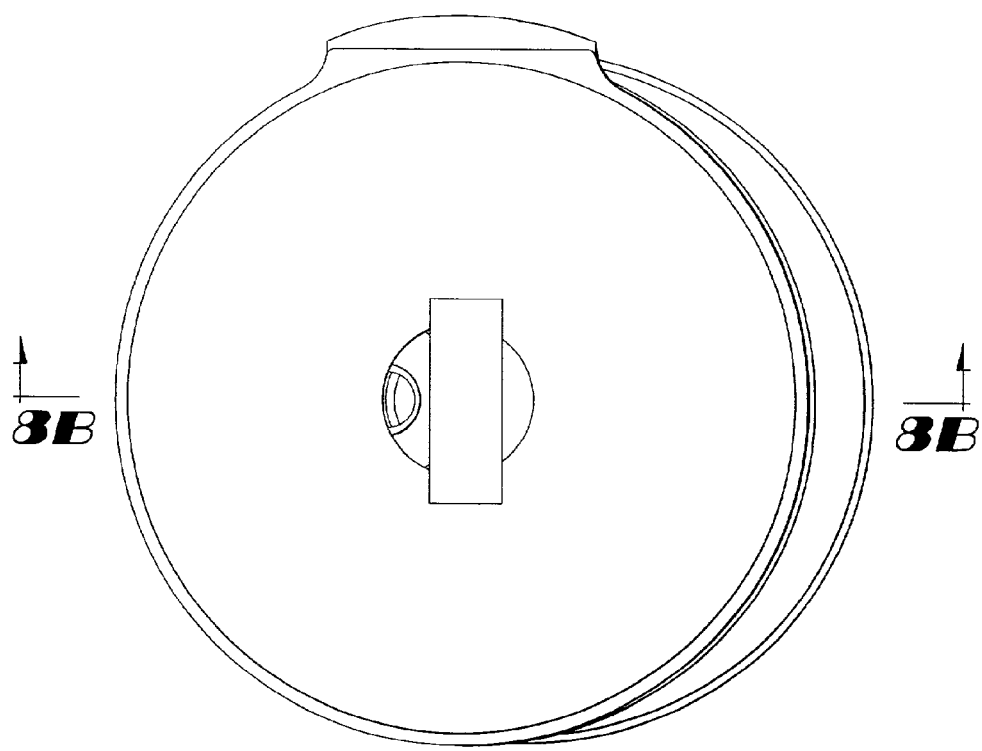
FIG. 8 is a plan view (A) and sectional view (B) of one embodiment of an intervertebral endoprosthesis of the invention undergoing lateral bending.
Figure 8B:
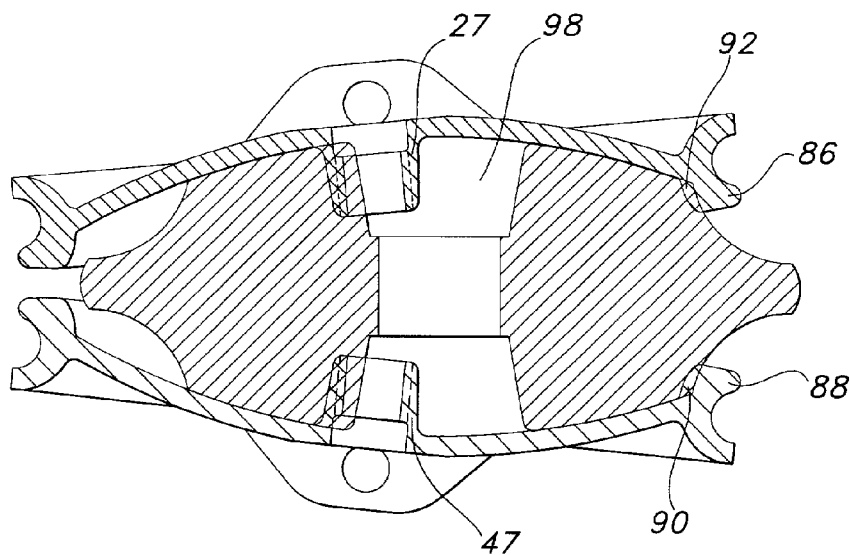
Figure 9A:
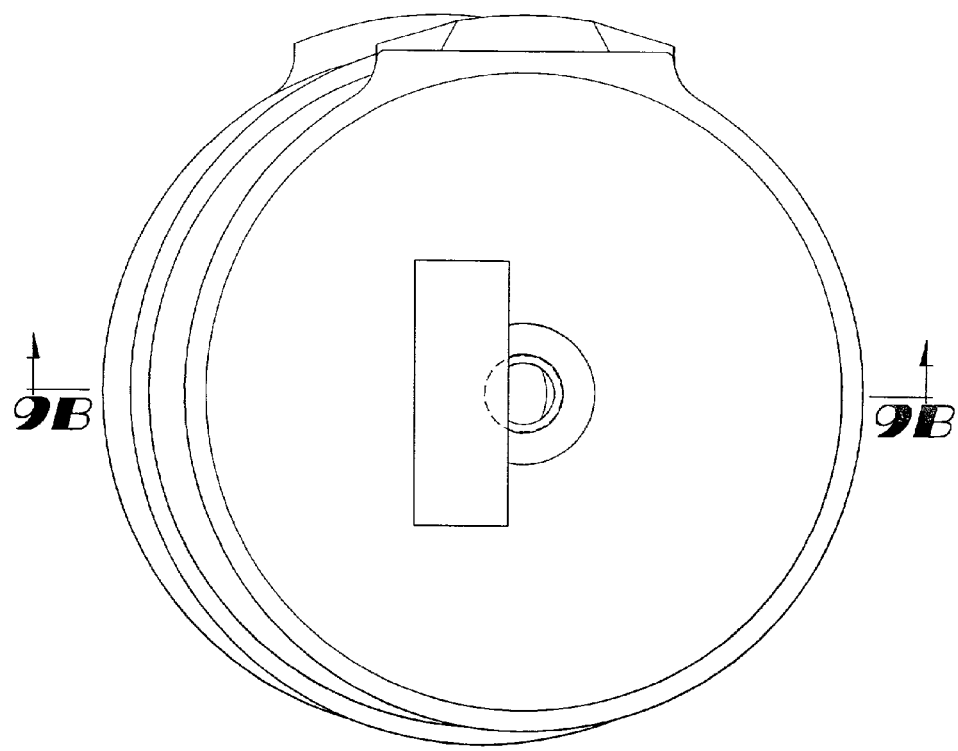
FIG. 9 is a plan view (A) and sectional view (B) of one embodiment of an intervertebral endoprosthesis of the invention undergoing translation.
Figure 9B:
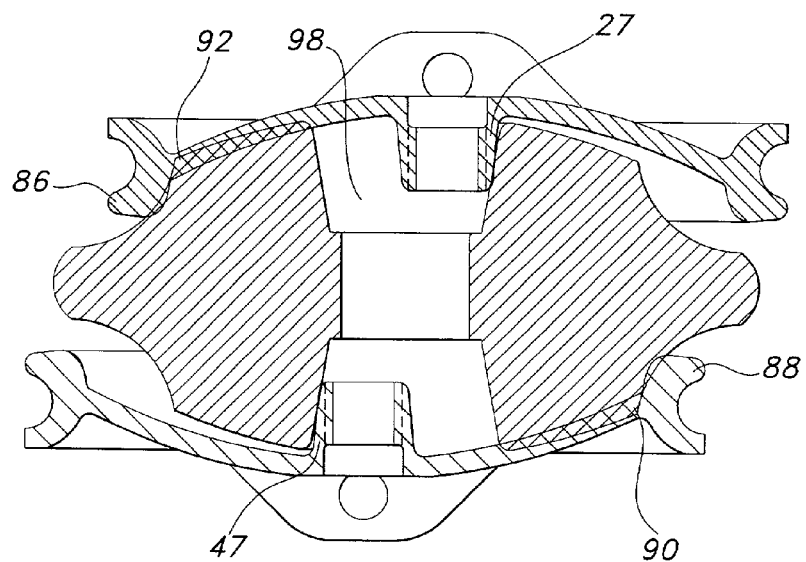

As can be seen best in the exploded view shown in FIG. 7, in accordance with this preferred embodiment, the present invention includes four main components: two shells 20, 40, a central body 60, and a sheath 70. The complete assembly of the device is shown in FIGS. 4 and 6, wherein the central body 60 is bracketed between shells 20, 40. The flexible sheath 70 extends between the two opposing shells 20, 40, and encapsulates the central body 60. As described in farther detail below, the geometric configuration of the shells 20, 40, the central body 60, and the sheath 70, are complementary. As such the geometric configuration of these components cooperate to (1) join the components into a unitary structure, and (2) define important functional features of the device.

Preferably, shells 20, 40 are cup-like so as to include an outer convex surface 23 and an inner concave surface 21, 41. The outer surfaces 23 can be coated with a nonspherical sintered bead coating 22, 42, or with some other coating that will promote bony ingrowth. The inner surfaces 21, 41 (shown in FIG. 6) are preferably very smooth, and may be machined or polished.

The shells, 20, 40 include a number of geometric features that as described in further detail below cooperate with other components of the devices. Specifically, these features include a central retaining post 27, 47, an outer circumferential groove 82, 84, and radial stop or an extension 86, 88. The central retaining post 27, 47 extends axially from inner surfaces 21, 41. In addition, each shell 20, 40 includes an edge 73, 74, respectively. The outer circumferential grooves 82, 84 extend into the edges 73, 73 of the shells 20, 40. As seen best in FIG. 6, the radial stops or extensions 86, 88 extend from the edge 73, 74 in a direction generally perpendicular to the general plane of the shells 20, 40.

Each shell may also be provided with tabs or flanges 25, 45. The tabs or flanges extend from a portion of the edge 73, 74 in a direction generally perpendicular to the general plane of the shells 20, 40, but in a direction generally opposite the radial stops or extensions 86, 88. The tabs or flanges 25, 45 help to prevent long-term migration within the disc space, as well as catastrophic posterior expulsion, and the resulting damage to the spinal cord, other nerves, or vascular structures. Insertion stops 25, 45 may contain openings 26, 46 that can releasably engage an insertion tool (not shown). The insertion tool will generally contain flexible prongs to releasably engage openings 26, 46. The insertion tool will also generally include a disengagement block that can press against the side of the implant once it has been properly positioned in the intervertebral space and force the openings 26, 46 off of the prongs of the tool. The shells can be made from any suitable biocompatible rigid material. In accordance with a preferred embodiment, the shells are made from a titanium alloy, and most preferably the titanium alloy is ASTM F-136. The bead coating 22, 42, however, is preferably made from ASTM F-67 pure titanium.

As shown best in FIG. 6, central body 60 is a preferably a donut-shaped structure, and includes a convex upper contact surface 94, a convex lower contact surface 96, and a central axial opening 98. In addition, central body member 60 preferably includes an upper shoulder 92 and a lower shoulder 90. Each shoulder 90, 92 consists of an indentation in the surface of the central body member which defines a ledge that extends around the circumference of the central body 60.

The central body 60 is both deformable and resilient, and is composed of a material that has surface regions that are harder than the interior region. This allows the central body to be sufficiently deformable and resilient that the implant functions effectively to provide resistance to compression and to provide dampening, while still providing adequate surface durability and wear resistance. In addition, the material of the central body has surfaces that are very lubricious, in order to decrease friction between the central body and the rigid opposing shells.

The material used to make the central body is typically a slightly elastomeric biocompatible polymeric material, which may be coated or impregnated to increase surface hardness, or lubricity, or both, as described above. Coating may be done by any suitable technique, such as dip coating, and the coating solution may be include one or more polymers, including those described below for the central body. The coating polymer may be the same as or different from the polymer used to form the central body, and may have a different durometer from that used in the central body. Typical coating thickness is greater than about 1 mil, more particularly from about 2 mil to about 5 mil. Examples of suitable materials include polyurethanes, such as polycarbonates and polyethers, such as Chronothane P 75A or P 55D (P-eth-PU aromatic, CT Biomaterials); Chronoflex C 55D, C 65D, C 80A, or C 93A (PC-PU aromatic, CT Biomaterials); ElastEon II 80A (Si-PU aromatic, Elastomedic); Bionate 55D/S or 80A-80A/S (PC-PU aromatic with S-SME, PTG); CarboSil-10 90A (PC-Si-PU aromatic, PTG); Tecothane TT-1055D or TT-1065D (P-eth-PU aromatic, Thermedics); Tecoflex EG-93A (P-eth-PU aliphatic, Thermedics); and Carbothane PC 3585A or PC 3555D (PC-PU aliphatic, Thermedics).

The last main component of this preferred embodiment of the present invention is the sheath 70. As show in FIG. 7, the sheath 70 is a tubular structure, and is made from a flexible material. The material used to make the sheath is typically biocompatible and elastic, such as a segmented polyurethane, having a thickness ranging from about 5 to about 30 mils, more particularly about 10-11 mils. Examples of suitable materials include BIOSPAN-S (aromatic polyetherurethaneurea with surface modified end groups, Polymer Technology Group), CHRONOFLEX AR/LT (aromatic polycarbonate polyurethane with low-tack properties, CardioTech International), CHRONOTHANE B (aromatic polyether polyurethane, CardioTech International), CARBOTHANE PC (aliphatic polycarbonate polyurethane, Thermedics).

As noted above, the various geometric features of the main components of this preferred embodiment of the present invention cooperate to join the components into a unitary structure. In general, the ends of the sheath 70 are attached to the shells, and the central body 60 is encapsulated between the shells 20, 40 and the sheath 70. More specifically, referring to FIG. 6, preferably the edges of flexible sheath 70 can overlap the outer circumferential grooves 82, 84 of the shells 20, 40. Retaining rings 71, 72 are then placed over the edges of the sheath 70 and into the circumferential grooves 82, 84, thereby holding the flexible sheath in place and attaching it to the shells. While any suitable biocompatible material can be used for the retaining rings, titanium or titanium alloys have been found to be particularly suitable. The retaining rings are desirably fixed in place by, e.g., welding the areas of overlap between the ends of the retaining rings. Because of the high temperatures needed to weld titanium and titanium alloys, and because of the proximity of the weld area to both the flexible sheath 70 and the central body 60, laser welding is typically used.

As also noted above, the various geometric features of the main components of the preferred embodiment of the present invention cooperate to define important functional features of the device. These features primarily include defining the kinematics of motion provided by the device, prohibiting expulsion of the central body 60, providing post assembly access to the interior of the device, providing an attachment mechanism for inserting the device, and providing a port for the insertion of lubricant into the implant cavity.

The kinematics of the motion provided by the prosthesis are defined primarily by the geometric interaction of the central body 60 and the shells 20, 40. Although the central body is encapsulated within the sheath and the shells, it is not attached to these components. Accordingly, the central body 60 freely moves within enclosed structure and is only constrained by geometric limitations. As seen best in FIG. 6, the concave shape of the inner surfaces 21, 41 of shells 20, 40 complements the convex surfaces 94, 96 of central body 60. As the shells 20, 40 glide across the convex surfaces 94, 96, relatively unconstrained translational, flexural, or extensional motion of shells 20, 40 with respect to central body 60 is achieved. When the desired limit of the range of motion is reached, extensions 86, 88 on shells 20, 40 are designed to contact shoulders 90, 92 on the central body 60. Specifically, the inner portion of the extension forms a circumferential ridge that limits the range of motion of the shells 20, 40 relative to the central body 60 by contacting central body shoulders 90, 92 at the end of the allowable range of motion. In an actual vertebral joint, this occurs at a joint flexion/extension of about ±10°, at lateral bending of about 11°, and/or at translation of about 2-3 mm.

As explained above, in one embodiment of the invention, the shells are concavo-convex, and their inner surfaces mated and articulated with a convex outer surface of the deformable resilient central body. The implant also contains a sheath or sleeve that is secured to the rims of the shells with retaining rings, and which, together with the inner surfaces of the shells, forms an implant cavity. In a particular aspect of this embodiment, using a coordinate system wherein the geometrical center of the implant is located at the origin, and assigning the x-axis to the anterior (positive) and posterior (negative) aspect of the implant, the y-axis to the right (positive) and left (negative) aspect of the implant, and the z-axis to the cephalad (positive) and caudal (negative) aspects of the implant, the convex portion of the outer surface and the concave portion of the inner surface of the shells can be described as a quadric surfaces, such that $$\frac{x^2}{a^2} + \frac{y^2}{b^2} + \frac{z^2}{c^2} = 1$$

where (±a,0,0), (0,±b,0), and (0,0,±c) represent the x, y, and z intercepts of the surfaces, respectively. Typical magnitudes for a, b, and c are about 11 mm, 30 mm, and 10 mm, respectively.

The implant is symmetrical about the x-y plane, and is intended to be implanted in the right-left center of the disc space, but may or may not be centered in the anterior-posterior direction. In any event, the implant is not allowed to protrude in the posterior direction past the posterior margin of the vertebral body.

As noted above, geometric features also serve to prevent the expulsion of the central body 60. In particular, this is achieved by the geometric interaction of the shells 20, 40 and the central body 60. Shells 20, 40 also contain central retaining posts 27, 47 which extend axially from inner surfaces 21, 41 into a central axial opening 98 in central body 60 and which stop central body 60 from being expelled from the implant during extreme flexion or extension. The diameter of central axial opening 98 is somewhat larger than the diameter of central retaining posts 27, 47. In the coordinate system described above, the central axis of the retaining post is typically coincident with the z-axis, but may move slightly to accommodate various clinical scenarios. The shape of the post may be any quadric surface. However, a truncated tapered elliptical cone is a particularly suitable geometry. Similarly, the geometry of the central axial opening of the central body will correspond to the geometry of the retaining post, and will have a similar geometry.

Also described above, the shells contain extensions or walls formed on the inner surface, for example around the edge of the shell, and that extend toward the deformable resilient central body. This extension or wall limits allowable translation of the deformable resilient central body with respect to the shell when the extension comes into contact with a shoulder formed on the surface of the central body, e.g., under shear loading of the implant. The height of the extension or wall should be less than about 2.5 mm in order to allow the full range of desired flexion/extension and right/left lateral bending motions.

The resilient deformable central body contains surfaces that are described by an equation similar to that for the inner surfaces of the shells, and which articulates with those inner surfaces. The central body will have a plane of symmetry if identical opposing shells are used. As described above, the central body also features an equatorial rim that acts as a "soft stop" in the event the patient participates in extreme activities that result in movements greater than the designed range of flexion/extension or lateral bending. In such a situation, the central body will have translated until the retaining post has contacted the inner surface of the central axial opening, and the extension or wall will have contacted the shoulder of the central body. Opposite the wall/shoulder contact, the edges of the shells will be in close proximity, but will be kept from contacting each other by contact with the equatorial rim of the central body. If desired, the thickness of the rim can be varied to further limit the range of motion.

Another important characteristic of this preferred embodiment of the present invention is the provision of a means for accessing the interior of the device after it has been assembled into a unitary structure. This means consists of a central axial opening included in the shells 20, 40. Typically, this opening will be provided through central retaining posts 27, 47. By providing access to the interior of the device, sterilization can be done just prior to implantation of the device. Sterilization is preferably accomplished by introducing an ethylene oxide surface sterilant. Caution should be exercised in using irradiation sterilization, as this can result in degradation of the polymeric materials in the sheath or central body, particularly if these include polyurethanes.

Figure 5:
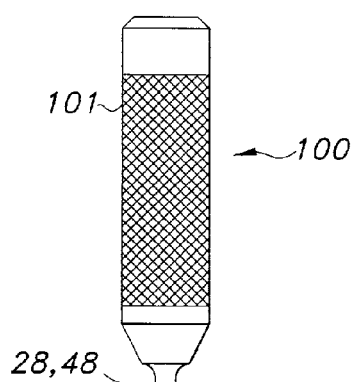
FIG. 5 is a plan view of an implant plug and plug installation tool used to insert a plug into an intervertebral endoprosthesis.

After sterilization, the central openings can be sealed using plugs 28, 48. Preferably, only one plug is inserted first. The plug is inserted using insertion tool 100, shown in FIG. 5, and which contains handle 101 and detachable integral plug 28, 48. The tool is designed so that plug 28, 48 detaches from the tool when a predetermined torque has been reached during insertion of the plug. The tool can then be discarded.

After one plug has been inserted to one of the shells, a lubricant 80 is preferably introduced into the interior of the device prior to inserting the second plug. To do this a syringe is used to introduce the lubricant into the remaining central opening, and the implant is slightly compressed to remove some of the excess air. Another insertion tool 100 is then used to insert a plug into that central opening, and thereby completely seal the interior of the device from its exterior environment. In accordance with the preferred embodiment of the present invention the lubricant 80 is saline. However, other lubricants may be used, for example, hyaluronic acid, mineral oil, and the like.

The two shells 20, 40 are virtually identical in shape and composition, however those of skill in the art will understand that it is possible to use shells of different sizes (including thicknesses), shapes, or materials, e.g., in order to provide a more customized fit to the patient's anatomy, and that this does not depart from the spirit and scope of the invention.

The deformable resilient central body is disposed between the opposed shells, as described above and illustrated in the drawing figures. Its upper and lower surfaces articulate with the upper and lower shells, respectively, and have a geometry that is similar to that of the shells.

Figure 10A:
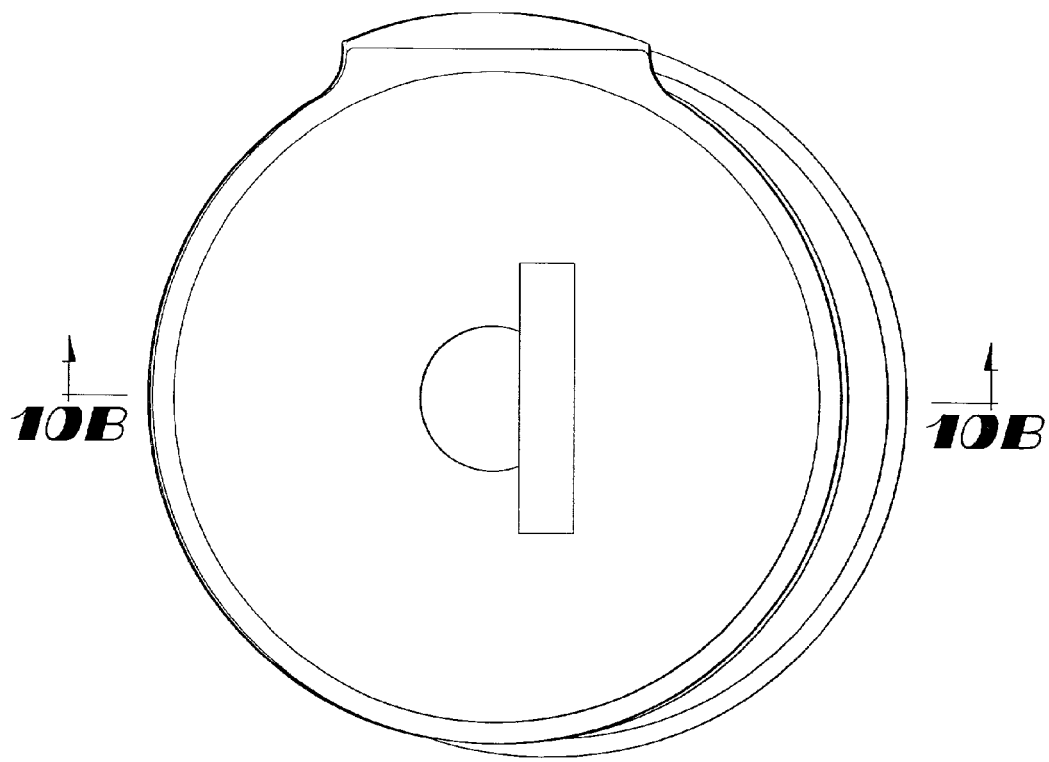
Figure 10B:
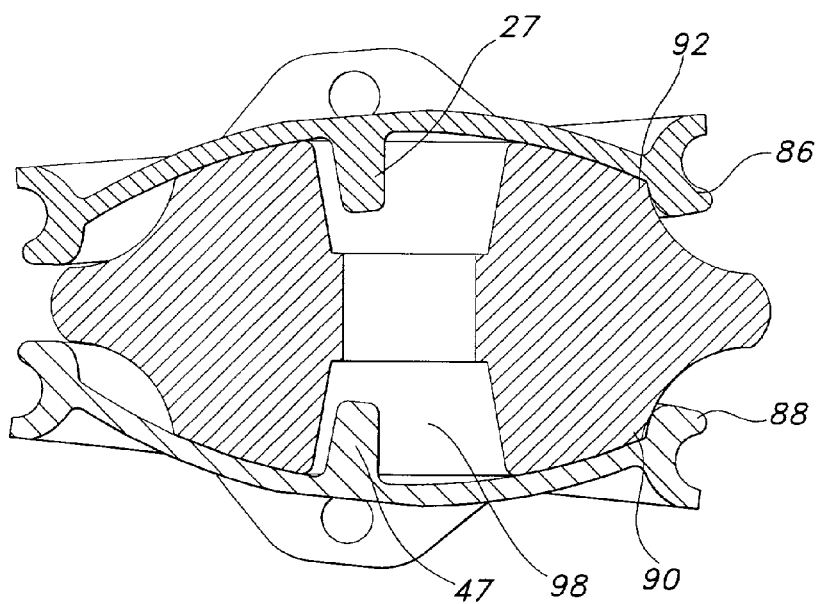
Figure 11A:
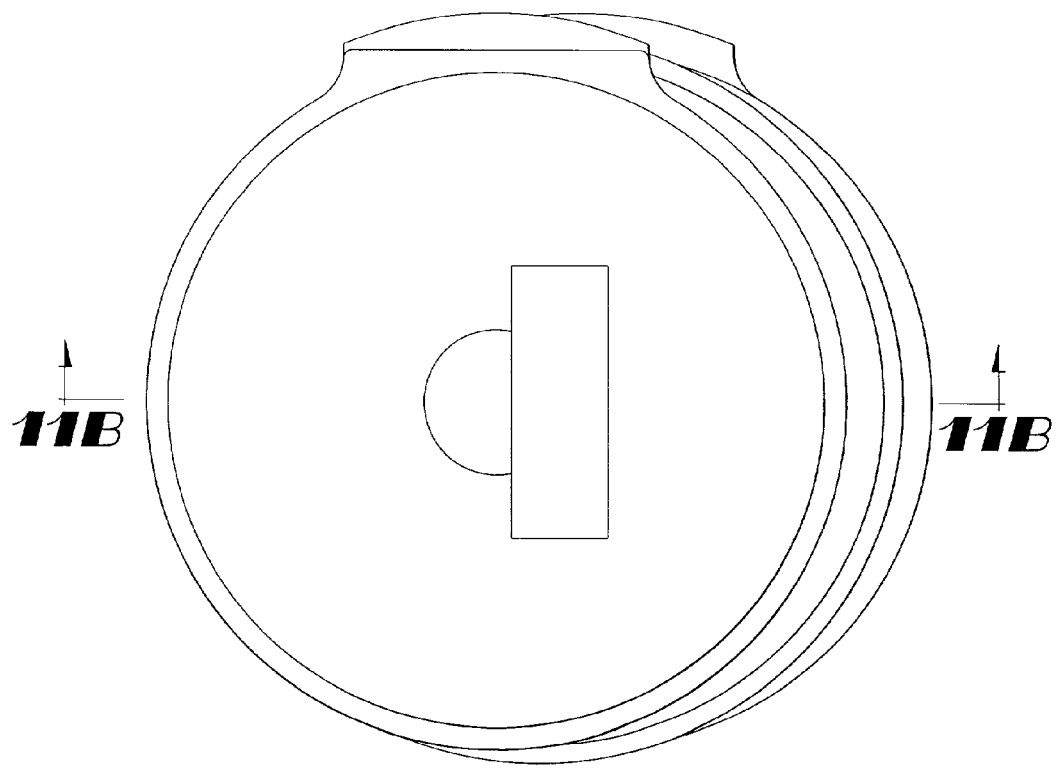
FIG. 11 is a plan view (A) and sectional view (B) of one embodiment of an intervertebral endoprosthesis of the invention undergoing translation.
Figure 11B:
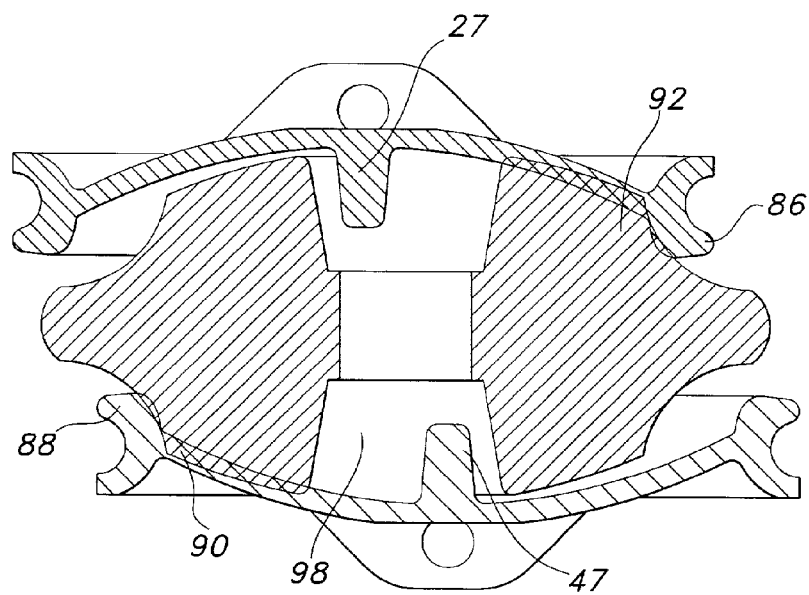

The kinematics of various embodiments of the implant are illustrated in FIGS. 8, 9, 10, and 11. FIG. 8A illustrates a plan view of an implant having a hollow central retaining post and undergoing lateral bending. The range of lateral bending is limited to about 11°, as indicated in FIG. 8B, which is a sectional view along line A-A of FIG. 8A. Contact of the walls or extensions 86, 88 of the shells with shoulders 90, 92 of the central body limit the range of motion to that desired. The central retaining posts 27, 47 may also contribute to limiting the range of motion by contact with the central axial opening of the central body. FIG. 9A illustrates a plan view of an implant of the type shown in FIG. 8 undergoing lateral translation. FIG. 9B shows a sectional view along line G-G. Again, the contact between walls or extensions 86, 88 of the shells and shoulders 90, 92 of the central body limit the range of motion to that desired, and central retaining posts 27, 47 may also contribute. FIGS. 10 and 11 provide similar plan and sectional views (along line H-H and I-I, respectively), illustrating a different embodiment of the implant (without a hollow central retaining post) undergoing lateral bending (FIG. 10) and lateral translation (FIG. 11). In each case, the range of motion is limited by contact between walls or extensions 86, 88 of the shells and shoulders 90, 92 of the central body.

As described above, the implant is desirably used as an endoprosthesis inserted between two adjacent vertebral bodies. The implant may be introduced using a posterior or anterior approach. For cervical implantation, an anterior approach is preferred. The implanting procedure is carried out after discectomy, as an alternative to spinal fusion. The appropriate size of the implant for a particular patient, determination of the appropriate location of the implant in the intervertebral space, and implantation are all desirably accomplished using precision stereotactic techniques, apparatus, and procedures, such as the techniques and procedures described in copending U.S. Ser. No. 09/783,860, filed on Feb. 13, 2001, the entire contents of which are hereby incorporated by reference. Of course, non-stereotactic techniques can also be used. In either case, discectomy is used to remove degenerated, diseased disc material and to provide access to the intervertebral space. This access is used to remove a portion of the vertebral body using a burr or other appropriate instruments, in order to provide access to the intervertebral space for a transverse milling device of the type described in U.S. Ser. No. 08/944,234, the entire contents of which are hereby incorporated by reference. The milling device is used to mill the surfaces of the superior and inferior vertebral bodies that partially define the intervertebral space to create an insertion cavity having surfaces that (a) complement the outer surfaces of the implant and (b) contain exposed cancellous bone. This provides for an appropriate fit of the implant with limited motion during the acute phase of implantation, thereby limiting the opportunity for fibrous tissue formation, and increases the likelihood for bony ingrowth, thereby increasing long-term stability.

The invention has been described above with respect to certain specific embodiments thereof. Those of skill in the art will understand that variations from these specific embodiments that ate within the spirit of the invention will fall within the scope of the appended claims and equivalents thereto.

What is claimed is:

1. A surgical implant suitable for use in a joint between the surfaces of two bones, comprising:
   two rigid opposing shells, each having
      an outer surface adapted to engage the surfaces of the bones of a joint in such a way that movement of the shell relative to the bone surface is resisted by friction between the outer surface and the surface of the bone;
      an inner surface that is smoother than the outer surface; and
      an edge between the outer surface and the inner surface;
   a deformable, resilient central body disposed between and slidable with respect to the inner surfaces of the shells, the central body comprising an outer surface, at least a portion of which has a shape that complements and articulates with the shape of the inner surfaces of both rigid opposing shells to allow the inner surfaces of the rigid opposing shells and the outer surface of the central body to move easily with respect to each other within a constrained range of motion, but to resist such movement outside the constrained range of motion, wherein an upper portion and a lower portion of the outer surface of the central body are harder than an interior region of the central body disposed between the upper and lower portions;
   a flexible sheath extending between edges of the opposing shells, having an inner surface that, together with the inner surfaces of the rigid shells, defines a cavity containing the central body; and a liquid lubricant, which occupies at least a portion of the cavity between the central body and the opposing shells.

2. The surgical implant of claim 1, wherein the edge of at least one of the rigid opposing shells comprises a tab extending axially away from the central body.

3. The surgical implant of claim 2, wherein the tab is adapted to releasably receive a tool for manipulating, inserting or removing the implant.

4. The surgical implant of claim 3, wherein the edges of both rigid opposing shells comprise a tab.

5. The surgical implant of claim 1, wherein the outer surface of each rigid opposing shell is cooled with a biocompatible porous coating.

6. The surgical implant of claim 5, wherein the porous coating comprises nonspherical sintered beads of a biocompatible metal or metal alloy.

7. The surgical implant of claim 6, wherein the rigid shell comprises a titanium alloy and wherein the porous coating comprises nonspherical sintered titanium beads.

8. A surgical implant suitable for use in a joint between the surfaces of two bones, comprising:
two rigid opposing shells, each having
an outer surface adapted to engage the surfaces of the bones of a joint in such a way that movement of the shell relative to the bone surface is resisted by friction between the outer surface and the surface of the bone;
an inner surface that is smoother than the outer surface; and
an edge between the outer surface and the inner surface;
wherein at least one of the rigid opposing shells further comprises a closable passage between its outer surface and its inner surface;
a deformable, resilient central body disposed between the inner surfaces of the shells comprising an outer surface, at least a portion of which has a shape that compliments and articulates with the shape of the inner surfaces of the rigid opposing shells to allow the inner surfaces of the rigid opposing shells and the outer surface of the central body to slidably move easily with respect to each other within a constrained range of motion, but to resist such movement outside the constrained range of motion; and
a lubricant positioned between the central body and the opposing shells;
wherein the closable passage is configured in a manner that permits the introduction of the lubricant into the implant between the central body and the opposing shells.

9. The surgical implant of claim 8, wherein the closable passage comprises a hole that is closable by insertion of a correspondingly sized plug.

10. A vertebral endoprosthesis, comprising:
an upper and a lower rigid, opposed, biocompatible shell, each comprising:
an outer, rough surface;
an inner, smooth concave surface; and
an edge between the surfaces;
wherein the inner smooth surface of at least one of the shells comprises a motion limiting device;
a deformable, resilient central body disposed between the inner, smooth concave surfaces of the upper and lower shells, comprising:
a smooth convex upper surface adjacent to the inner smooth concave surface of the upper shell and a smooth convex lower surface adjacent to the inner smooth concave surface of the lower shell, the upper and lower surfaces being harder than an interior region of the central body disposed between the upper and lower surfaces; and a motion limiting device disposed on at least one of the smooth convex upper and lower surfaces adapted to contact the motion limiting device of the inner surface and limit the relative motion of the shell with respect to the central body; and
an elastic sheath disposed between the upper and lower shells and external to the central body, comprising an inner surface, an outer surface, an upper edge attached to the upper shell, and a lower edge attached to the lower shell; wherein the inner surface of the sheath and the inner surfaces of the shells define an enclosed cavity receiving the central body; and
a lubricant disposed within the enclosed cavity surrounding the central body.

11. The vertebral endoprosthesis of claim 10, wherein the motion limiting device on the shell comprises a first ridge disposed on the inner surface of the shell, and the motion limiting device on the central body comprises a shoulder disposed on the surface of the central body.

12. The vertebral endoprosthesis of claim 11, wherein the first ridge comprises an axial extension of at least a portion of the edge of the shell toward the central body, and circumscribes the area of the inner surface that can contact the smooth convex surface of the central body.

13. The vertebral endoprosthesis of claim 11, wherein the shoulder circumscribes the convex surface of the central body.

14. The vertebral endoprosthesis of claim 10, wherein the outer surface of the shell is convex.

15. The vertebral endoprosthesis of claim 10, wherein the outer surface of the shell comprises a porous biocompatible coating.

16. The vertebral endoprosthesis of claim 15, wherein the porous biocompatible coating comprises nonspherical sintered beads of a biocompatible metal.

17. The vertebral endoprosthesis of claim 10, wherein the edge of at least one of the shells comprises a circumferential groove adapted to be overlapped by a sheath and to receive a retaining ring securing the sheath to the shell.

18. The vertebral endoprosthesis of claim 17, further comprising a retaining ring disposed in the circumferential groove, and compressing the edge of the sheath into the groove.

19. The vertebral endoprosthesis of claim 18, wherein the retaining ring comprises a wire or filament of biocompatible material, formed into a ring.

20. The vertebral endoprosthesis of claim 19, wherein the ends of the ring are laser welded.

21. The vertebral endoprosthesis of claim 10, wherein the edge of at least one of the shells comprises an tab extending axially away from the central body.

22. The vertebral endoprosthesis of claim 21, wherein the tab is adapted to releasably engage a tool for manipulating or inserting the endoprosthesis.

23. The vertebral endoprosthesis of claim 22, wherein the tab comprises an opening to releasably receive a retaining prong of the tool.

24. The vertebral endoprosthesis of claim 10, wherein the inner surface of at least one shell comprises a post extending toward the central body, and wherein the outer surface of the central body comprises at least one opening adapted to receive the post.

25. The vertebral endoprosthesis of claim 10, wherein at least one of the shells further comprises a closable passage between its outer surface and its inner surface.

26. The vertebral endoprosthesis of claim 25, wherein the closable passage comprises a hole that is closable by insertion of a correspondingly sized plug.

27. The vertebral endoprosthesis of claim 26, wherein the hole and plug are threaded with complementary threads.

28. A vertebral endoprosthesis, comprising:
an upper and a lower rigid, opposed biocompatible concavo-convex shell, each comprising:
an outer, rough convex surface, comprising a porous coating of a biocompatible material;
an inner concave surface, comprising:
a smooth contact area; and
an axial post extending toward the opposing shell; and
an edge between the surfaces, comprising:
a circumferential groove adapted to receive a retaining ring; a first ridge circumscribing the contact area of the inner concave surface and extending axially toward the opposing shell;
a tab extending axially away from the opposing shell, and comprising an opening adapted to releasably engage a tool for manipulating, inserting, or removing the endoprosthesis;
a closable passage between the outer surface and the inner surface of the shell;
a deformable, resilient central body disposed between the inner, smooth concave surfaces of the upper and lower shells, comprising:
smooth convex upper and lower surfaces complementary and adjacent to the smooth contact area of the inner surfaces of the respective upper and lower shells;
a shoulder circumscribing each of the smooth convex upper and lower surfaces and adapted to contact the first ridge of the adjacent shell and limit the relative motion of the shell with respect to the central body; a laterally extending equatorial ridge disposed between the first ridge of the upper concavo-convex shell and the first ridge of the lower concavo-convex shell;
an opening in the upper and lower convex contact surfaces adapted to receive the axial post of the inner surface of each shell;
an elastic sheath disposed between the upper and lower shells and external to the central body, comprising an inner surface, an outer surface, an upper edge attached to the upper shell, and a lower edge attached to the lower shell, wherein the inner surface of the sheath and the inner surfaces of the shells define an enclosed cavity;
an upper retaining ring of a biocompatible material disposed in the circumferential groove in the upper concavo-convex shell and securing the upper edge of the elastic sheath to the shell and a lower retaining ring of a biocompatible material disposed in the circumferential groove of the lower concavo-convex shell and securing the lower edge of the sheath to the shell a plug of biocompatible material disposed in the closable passages between the outer surface and inner surface of at least one of the concavo-convex shells; and
a lubricant disposed within the implant cavity.

29. The vertebral endoprosthesis of claim 28, wherein a plug is disposed in the closable passage of each concavo-convex shell.

30. The endoprosthesis of claim 28 wherein the outer porous coating of biocompatible material is disposed to promote bony ingrowth.

31. The endoprosthesis of claim 28 wherein the outer porous coating of biocompatible material is formed by vacuum sintering.

32. The endoprosthesis of claim 28 wherein the outer porous coating is a titanium coating.

33. The implant of claim 32 wherein the outer porous, titanium coating meets ASTM F-67.

34. A bone joint implant comprising
two shells interconnected by a sleeve to form a cavity therein,
a central body having at least one indentation therein positioned within the cavity,
wherein at least one of the shells includes a retaining post that extends into the indentation and a lubricant within the cavity between the central body and the two shells;
wherein at least one of the shells includes an opening to allow introduction of the lubricant into the cavity, wherein the opening is sealed with a plug tool having a handle and a detachable integral plug associated therewith after introduction of the lubricant into the cavity.

35. The implant of claim 34 wherein the plug detaches from the tool when a predetermined torque has been reached during insertion of the plug into the opening.

36. A method of introducing the lubricant into a bone joint implant comprising two shells interconnected by a sleeve to form a cavity therein, and a central body having at least one indentation therein positioned within the cavity, wherein at least one of the shells includes a retaining post that extends into the indentation, and wherein both of the shells include an opening to allow introduction of a lubricant into the cavity, the method comprising:
(1) sealing one of the openings, (2) slightly compressing the implant to remove excess air, (3) injecting the lubricant into the unsealed opening, and (4) sealing the second opening.

37. The method of claim 36 wherein the openings in the shells are sealed using a seal plug tool having a segment designed to disengage at a predetermined torque.

* * * * *

UNITED STATES PATENT AND TRADEMARK OFFICE
CERTIFICATE OF CORRECTION

PATENT NO. : 7,641,692 B2 Page 1 of 1
APPLICATION NO. : 09/924298
DATED : January 5, 2010
INVENTOR(S) : Bryan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1827 days.

Signed and Sealed this

Sixteenth Day of November, 2010

David J. Kappos
*Director of the United States Patent and Trademark Office*